(12) United States Patent
Homer

(10) Patent No.: US 12,161,588 B2
(45) Date of Patent: *Dec. 10, 2024

(54) APPLICATION OF ELECTROMAGNETIC RADIATION TO THE HUMAN IRIS

(71) Applicant: Stroma Medical Corporation, Irvine, CA (US)

(72) Inventor: Gregg Homer, Irvine, CA (US)

(73) Assignee: Stroma Medical Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,244

(22) Filed: Sep. 19, 2023

(65) Prior Publication Data

US 2024/0009030 A1  Jan. 11, 2024

Related U.S. Application Data

(63) Continuation of application No. 17/732,287, filed on Apr. 28, 2022, now Pat. No. 11,806,282, which is a continuation of application No. 13/870,947, filed on Apr. 25, 2013, now abandoned, which is a continuation-in-part of application No. 13/456,111, filed on Apr. 25, 2012, now Pat. No. 10,744,034.

(51) Int. Cl.
| | |
|---|---|
| *A61F 9/008* | (2006.01) |
| *A61H 23/00* | (2006.01) |
| *A61B 18/20* | (2006.01) |
| *A61B 90/00* | (2016.01) |

(52) U.S. Cl.
CPC .......... *A61F 9/008* (2013.01); *A61F 9/00814* (2013.01); *A61F 9/00825* (2013.01); *A61H 23/00* (2013.01); *A61B 2018/205545* (2017.05); *A61B 2090/049* (2016.02); *A61F 2009/00846* (2013.01); *A61F 2009/00863* (2013.01); *A61F 2009/00876* (2013.01); *A61F 2009/00878* (2013.01); *A61F 2009/00891* (2013.01); *A61F 2009/00897* (2013.01)

(58) Field of Classification Search
CPC .. A61F 2009/00876; A61F 2009/00897; A61F 2009/00895; A61F 2009/00891
See application file for complete search history.

(56) References Cited

U.S. PATENT DOCUMENTS

| | | | | |
|---|---|---|---|---|
| 2005/0049584 | A1* | 3/2005 | Homer | A61F 9/00817 606/33 |
| 2012/0259321 | A1* | 10/2012 | Vera | A61F 9/00781 606/6 |

* cited by examiner

Primary Examiner — Lynsey C Eiseman
Assistant Examiner — Skylar Lindsey Christianson
(74) Attorney, Agent, or Firm — Foley & Lardner LLP

(57) ABSTRACT

Rather than rely solely upon pupillary occlusion or tracking of eye movement to protect the fundus from accidental exposure to electromagnetic radiation, the present invention also utilizes an electromagnetic radiation pathway with a profile such that the energy density at the iris is greater than the energy density at the posterior portion of the eye. This disparity in energy density allows for efficacy at the anterior iris treatment site, without injury to the fundus.

39 Claims, 6 Drawing Sheets

APPLICATION OF ELECTROMAGNETIC RADIATION TO THE HUMAN IRIS

CROSS-REFERENCE TO RELATED APPLICATIONS

This application is a continuation of U.S. patent application Ser. No. 17/732,287, filed Apr. 28, 2022, which is a continuation of U.S. patent application Ser. No. 13/870,947, filed Apr. 25, 2013, which is a continuation-in-part of U.S. patent application Ser. No. 13/456,111, filed Apr. 25, 2012. The content of the foregoing applications is incorporated herein in its entirety by reference.

BACKGROUND OF THE INVENTION

There are several new ophthalmic procedures that require the uniform application of electromagnetic radiation to a large portion of the human iris. Examples of these procedures include the method of laser eye-color change described in U.S. Pat. No. 6,912,528 (issued Jun. 28, 2005) and U.S. Pat. No. 8,206,379 (issued Jun. 26, 2012), issued to Applicant, and the method of glaucoma treatment described in U.S. patent application Ser. No. 13/456,111, filed by Applicant. Another example of these procedures is a novel treatment for presbyopia developed by Applicant whereby electromagnetic radiation is applied to the portion of the iris anterior to the pupillary constrictor muscles, thereby reducing the size of the pupil and increasing the depth of field of the patient's visual acuity.

The uniform application of electromagnetic radiation to the iris typically requires the use of a computerized scanning system to direct the electromagnetic radiation pathway across the iris in a pre-determined pattern.

The application of electromagnetic radiation to a large portion of the human iris poses a substantial risk of accidental exposure of electromagnetic radiation to the inside of the ocular orbit, including the fundus (which includes the includes the retina, optic disc, macula, fovea, and posterior pole). Exposure to these areas can cause permanent vision impairment or loss.

Several methods already exist to protect the fundus against accidental exposure from electromagnetic radiation. One such method comprises the occlusion of the pupil during the application of electromagnetic radiation to the anterior iris. By way of example, in U.S. Pat. No. 8,206,379, Applicant discloses the application to the iris of a contact lens bearing a physical occlusion to block the electromagnetic radiation pathway as it moves across the anterior iris. Another method is to establish a predetermined application pattern that avoids the pupil, track any movement of the eye during treatment, and either suspend or interrupt exposure (passive tracking) or shift the position of the treatment pattern (active tracking) in the event the eye moves. Passive and active eye tracking technologies are well-known in the art and readily commercially available. By way of example, SensoMotoric Instruments GmbH (Teltow, German) integrates its SMI Surgery Guidance active eye-tracking technology into computer-guided laser systems for such procedures as corneal surgery intraocular lens implant surgery. Another example is the OneK+ active eye tracker from Chronos Vision GmbH (Berlin, Germany) for use in connection with computer-guided laser refractive eye surgeries. The problem with these methods for mitigating the risk of accidental fundus exposure is that none of them can guarantee success 100% of the time. Contact lenses can move during surgery, thereby leaving the pupil unprotected and the fundus subject to accidental exposure. Eye tracking, while now highly advanced, are susceptible to mechanical and calculation errors that could result in fundus exposure. Moreover, the response time of eye tracking systems are often not fast enough to shift the treatment pattern before accidental exposure occurs.

A need thus exists for a device that provides uniform application of electromagnetic radiation to the anterior surface of the human iris through the use of a computer-guidance system, without subjecting the fundus to accidental exposure.

BRIEF SUMMARY OF THE INVENTION

Rather than rely solely upon pupillary occlusion or tracking of eye movement to protect the fundus from accidental exposure to electromagnetic radiation, the present invention also utilizes an electromagnetic radiation pathway with a profile such that the energy density at the iris is greater than the energy density at the posterior portion of the eye. This disparity in energy density allows for efficacy at the anterior iris treatment site, without injury to the fundus.

In one embodiment of the invention, the electromagnetic radiation comprises light waves. In one version of this embodiment, the electromagnetic radiation generator is a laser and the electromagnetic radiation pathway is a laser beam. The computerized scanning system applies the laser beam to the anterior surface of the iris. The profile of the laser beam is Gaussian, such that the beam profile converges to a focal point and then diverges from that focal point. Due to the profile of the laser beam, the energy density at the anterior iris is greater than the energy density at the fundus. In independent alternate versions of this embodiment, the divergence angle of the beam is 1.0-2.5 degrees, 2.5-5.0 degrees, 5.0-7.5 degrees, 7.5-10.0, 10.0-12.5 degrees, 12.5-15.0 degrees, 15.0-20.0 degrees, or greater than 20.0 degrees.

Computerized scanning systems are well-known in the art. The scanning system can be implemented using one or more computer systems. An exemplary computer system can include software, monitor, cabinet, keyboard, and mouse. The cabinet can house familiar computer components, such as a processor, memory, mass storage devices, and the like. The beam may be guided in any shape or pattern, including, without limitation, a spiral pattern, a raster pattern, or a segregated regional pattern.

In another version of the foregoing embodiment, the anterior iris is divided into two treatment zones, each zone being concentric to the pupil. The first treatment zone extends approximately from the outer periphery of the pupillary constrictor muscles to the outer periphery of the pupil. The second treatment zone extends approximately from the limbus to the outer periphery of the pupillary constrictor muscles. The computerized scanning system applies the laser beam first to the first treatment zone, in a spiral pattern, from the outer periphery to the inner periphery, and second to the second treatment zone, in a spiral pattern, from the outer periphery to the inner periphery.

In another embodiment of the invention, the electromagnetic radiation comprises sound waves. In one version of this embodiment, the electromagnetic radiation generator is a sound amplification by stimulated emission of radiation (or SASER), and the electromagnetic radiation pathway is a SASER beam. The computerized scanning system applies the SASER beam to the anterior surface of the iris. The profile of the SASER beam is Gaussian, such that the beam profile converges to a focal point and then diverges from that focal point. Due to the profile of the SASER beam, the energy density at the anterior iris is greater than the energy density at the fundus.

In another embodiment of the invention, an application of electromagnetic radiation overlaps a previous application of electromagnetic radiation within a 24-hour period. In the laser embodiment above, for example, a laser spot is applied in a manner that overlaps a previously applied laser spot within a 24-hour period. In another embodiment, an application of electromagnetic radiation is applied in a manner that does not overlap any previous application of electromagnetic radiation within a 24-hour period. In the laser embodiment above, a laser spot is applied in a manner that does not overlap any previously applied laser spot within a 24-hour period. In yet another embodiment, an application of electromagnetic radiation leaves an area of untreated iris between said application and all previous applications of electromagnetic radiation within a 24-hour period. In the laser embodiment above, a laser spot is applied in a manner that leaves an area of untreated iris between such spot and all previously applied laser spots within a 24-hour period. And in a further embodiment, some electromagnetic radiation applications overlap previous applications, and others do not, in a 24-hour period. In the laser embodiment above, some laser spots overlap previous laser spots, and others do not, within a 24-hour period.

In another embodiment of the invention, the device includes an apparatus to restrict movement of the head during the procedure. In one version of this embodiment, movement of the head is restricted using a surgical head restrain. Surgical head restrains are well-known in the art. In another version of this embodiment, a bite bar is used to restrict movement of the head during the procedure. Use of a bite bar to restrict head movement is well-known in the art, including the use of a bite bar during brain imaging. In yet another version of this embodiment, a head fixation target is used to restrict head movement of the head during the procedure. The head fixation target is a novel device invented by Applicant. It utilizes one or more rods, bars, or straps, made of any metal, fabric, plastic, or any other material, material, to apply pressure to predetermined points on the patient's head, thereby providing feedback to the patient with respect to any movement.

In another embodiment of the invention, the device includes an apparatus to restrict movement of the eye during the procedure. In one version of this embodiment, movement of the eye is restricted using a suction ring. Ophthalmic suction rings are well-known in the art. In another version, movement is restricted using a gaze fixation target. Gaze fixation is well-known in the art. Gaze fixation can utilize any object of fixation, including, without limitation, a three-dimensional object, a two-dimensional image, or a light. In one novel variation on this version of this embodiment invented by Applicant, a light source is placed at the end of a tube, such that the patient must look through the tube in order to see the light source. In addition to providing a gaze fixation target, this variation also provides a head fixation target because if the patient's moves off axis, the light source will no longer be visible. In another novel variation on this version of this embodiment invented by Applicant, the light produced by the light source changes colors during the procedure. The light might, for example, cycle among amber, red, green, white, and yellow. A color-changing fixation target is less likely to induce involuntary saccadic or other movement of the eye in order to refresh the image on the retina or, alternatively, the discomfort that comes with suppressing such movement. In another novel variation on this version of this embodiment invented by Applicant, the light produced by the light source changes intensity during the procedure. The light might, or example, cycle among bright, medium, and dim. An intensity-changing fixation target is also less likely to induce involuntary saccadic or other movement of the eye in order to refresh the image on the retina or, alternatively, the discomfort that comes with suppressing such movement. In still another novel variation on this version of this embodiment invented by Applicant, the fixation target comprises a moving image, which image may be animated or live action, in color or in black and white, in two- or three-dimensions. A moving image fixation target is also less likely to induce involuntary saccadic or other movement of the eye in order to refresh the image on the retina or, alternatively, the discomfort that comes with suppressing such movement. Any of these embodiments, variations, or versions may be placed in front of the treated eye or the fellow eye during the procedure in order to achieve fixation of the treated eye.

In another embodiment of the invention, the device includes an apparatus to detect movement of the eye during treatment. In one version of this embodiment, active eye tracking is used, whereby movement of the eye is identified, and the electromagnetic pathway is moved to correspond to the movement of the eye. These movements may consist of shifts along the anterior surface of the iris (along the so-called x-y plane), shifts in depth (along the so-called z axis), rotations around the orbital axis, or otherwise. Active eye tracking is well-known in the art. In another version of this embodiment, passive eye tracking is used, whereby movement of the eye is identified, and the electromagnetic radiation pathway is terminated or suspended. In a novel variation on this version of this embodiment invented by Applicant, movement of the eye is identified, and the electromagnetic radiation pathway is suspended until the eye returns to its previous position or assumes some other desired position, at which time the electromagnetic radiation pathway is resumed. In independent alternate variations on these versions of this embodiment, the electromagnetic radiation pathway is terminated or suspended by (a) terminating or suspending the power to the electromagnetic radiation source, (b) turning off the electromagnetic radiation source, (c) redirecting the electromagnetic radiation pathway away from the target area, (d) utilizing a shutter, baffle, shield, or other occluding device to interrupt the electromagnetic radiation pathway, or (e) utilizing a optical modulator (such as an acousto-optical modulator or an electro-optical modulator) or other energy modulator to interrupt the electromagnetic radiation pathway.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
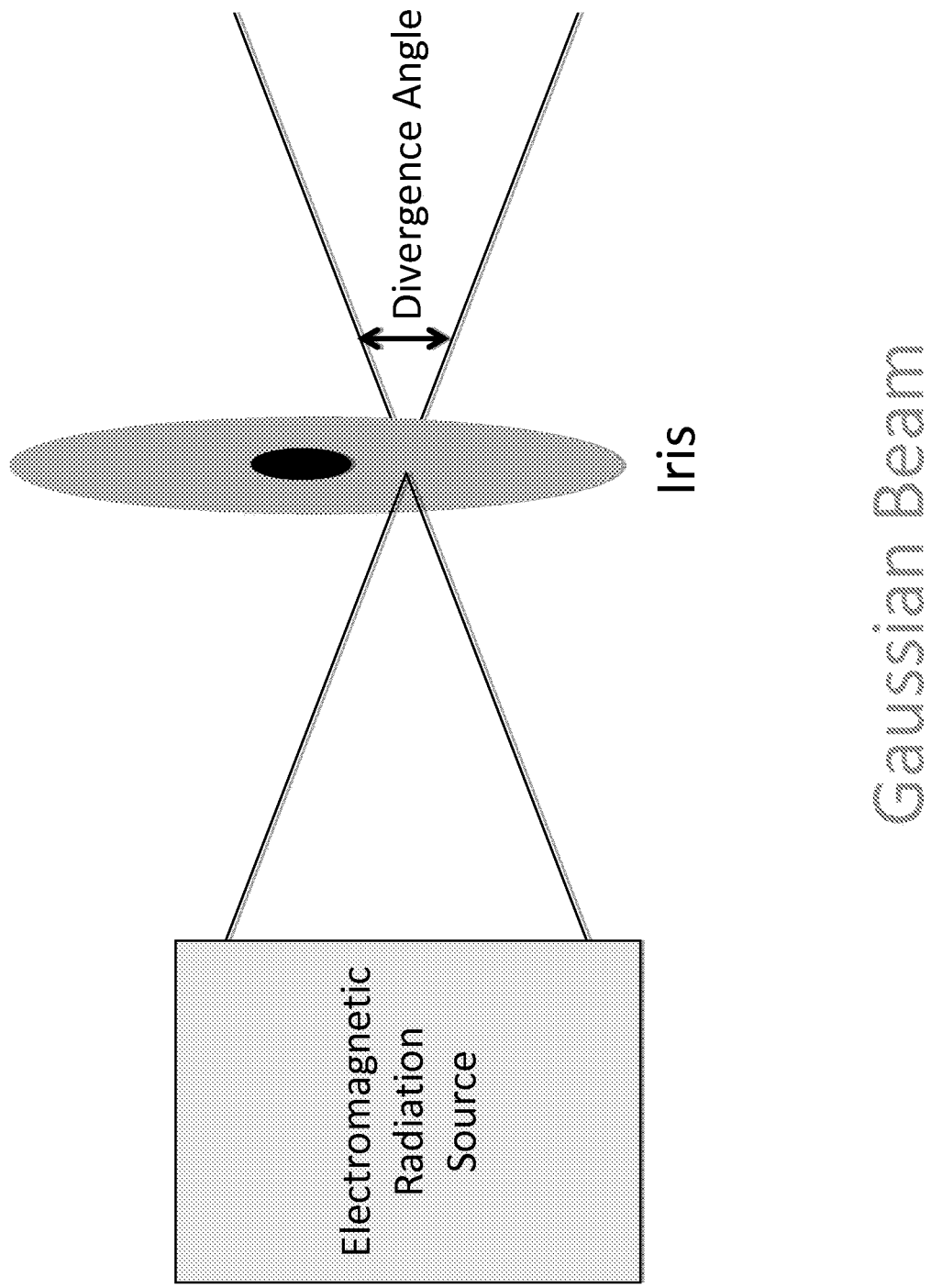
FIG. 1 shows aspects of an embodiment of the invention wherein the profile of the electromagnetic radiation pathway is such that the energy density at the iris is greater than the energy density at the posterior portion of the eye.

Rather than rely solely upon pupillary occlusion or tracking of eye movement to protect the fundus from accidental exposure to electromagnetic radiation, the present invention also utilizes an electromagnetic radiation pathway with a profile such that the energy density at the iris is greater than the energy density at the posterior portion of the eye. See, e.g., FIG. 1. This disparity in energy density allows for efficacy at the anterior iris treatment site, without injury to the fundus.

As used in this disclosure, "electromagnetic radiation" includes any form of electromagnetic radiation, whether in the form of sound, heat, light, or otherwise, and whether consisting of radio frequency, ultrasound, microwave, infrared, visible light, ultraviolet, x-ray, t-ray, gamma ray, or otherwise. The term "electromagnetic radiation" is not intended to restrict the form of radiation in terms of monochromaticity (i.e., composed of one or more than one different wavelength), directionality (i.e., produce a single non-divergent spot or radiate in several different directions), or coherence (i.e., the waves produced consist of a single phase relation or of multiple phase relations). Moreover, the frequency of the electromagnetic radiation can be any frequency within the electromagnetic spectrum, including, without limitation, extremely low frequency sound radiation (with a frequency of 3 Hz) to gamma radiation (with a frequency of 300 EHz). The electromagnetic radiation can be delivered in a continuous wave or in pulses, and the pulse width may be any time interval, including microseconds, nanoseconds, picoseconds, femtoseconds, or attoseconds. If pulsed, any repetition rate may be used, including, without limitation, repetition rates from 1 Hz to 100 THz. In addition, any energy output may be used, and any energy density may be created at the target treatment side, including, without limitation, energy outputs from 1 W to 1000 W. Finally, any gain medium may be used, including, without limitation, glass, solid, liquid, gas, crystal, or semiconductor. In the case of laser energy, the specific gain media may comprise Nd:YAG, alexandrite, pulsed-dye, or any other medium.

The term "laser" includes any form of radiation within the light spectrum, whether consisting of infrared, visible light, ultraviolet, or otherwise. The term "laser" is not intended to restrict the form of radiation in terms of monochromaticity (i.e., composed of one or more than one different wavelength), directionality (i.e., produce a single non-divergent spot or radiate in several different directions), or coherence (i.e., the waves produced consist of a single phase relation or of multiple phase relations). The laser radiation can be delivered in a continuous wave or in pulses, and the pulse width may be any time interval, including microseconds, nanoseconds, picoseconds, femtoseconds, or attoseconds. If pulsed, any repetition rate may be used, including, without limitation, repetition rates from 1 Hz to 100 THz. In addition, any energy output may be used, and any energy density may be created at the target treatment side, including, without limitation, energy outputs from 1 W to 1000 W. Finally, any gain medium may be used, including, without limitation, glass, solid, liquid, gas, crystal, or semiconductor, and, more specifically, Nd:YAG, alexandrite, pulsed-dye, or any other medium.

The term "pathway" includes any electromagnetic radiation pathway, such as a laser beam, radio frequency pathway, SASER pathway, ultrasound pathway, microwave pathway, infrared pathway, visible light pathway, ultraviolet pathway, x-ray pathway, t-ray pathway, gamma ray pathway, or otherwise. In addition, the electromagnetic radiation may be fully collimated or any drainage angle of divergence or convergence. Finally, the term "pathway" should be understood to include a single pathway or multiple pathways, and the multiple pathways may result from the splitting or screening of a single pathway or the generation of multiple pathways with multiple frequencies, shapes, energy densities, and other characteristics. If the pathway is a laser beam, it may or may not be fired through a goniolens.

The term "spot" includes the plane of intersection between the pathway and the target cells or tissue, such as the laser spot, radio frequency site, SASER site, ultrasound site, microwave site, infrared site, visible light site, ultraviolet site, x-ray site, t-ray site, gamma ray site, or otherwise. The term "electromagnetic radiation" is not intended to limit the pathway or spot to any particular shape, size, or angle of projection. Spots can be tangent, overlapped, or isolated, and overlapping may occur in any direction (x, y, or z). They can also be square, rectangular, circular, elliptical, triangular, trapezoidal, torus, or otherwise. Finally, a spot can measure any diameter, including, without limitation, 1-10 microns, 10-50 microns, 50-100 microns, 100-200 microns, 200-500 microns, 500-1,000 microns, or 1,000 microns to 15 millimeters.

Preferably, the energy density of the pathway is set to a level that minimizes any unwanted damage to the ocular tissue. Although the preferred electromagnetic radiation frequencies will pass through the cornea without causing any corneal injury, the method of the present invention can further include creating an opening in the cornea before applying the electromagnetic radiation. Once the opening has been created, the electromagnetic radiation may be introduced directly through the opening or via a pathway-conducting vehicle, such as light-conducting fiber. If necessary, a temporary contact lens can be applied to reduce post-operative discomfort.

In one embodiment of the invention, the electromagnetic radiation comprises light waves. In one version of this embodiment, the electromagnetic radiation generator is a laser and the electromagnetic radiation pathway is a laser beam. The computerized scanning system applies the laser beam to the anterior surface of the iris. The profile of the laser beam is Gaussian, such that the beam profile converges to a focal point and then diverges from that focal point. See FIG. 1. Due to the profile of the laser beam, the energy density at the anterior iris is greater than the energy density at the fundus. In independent alternate versions of this embodiment, the divergence angle of the beam is 1.0-2.5 degrees, 2.5-5.0 degrees, 5.0-7.5 degrees, 7.5-10.0, 10.0-12.5 degrees, 12.5-15.0 degrees, 15.0-20.0 degrees, or greater than 20.0 degrees. In further independent alternate versions of this embodiment, the spot produced by the laser beam on the anterior surface of the iris has a diameter of 1-10 microns, 10-50 microns, 50-100 microns, 100-200 microns, 200-500 microns, 500-1,000 microns, and 1,000 microns to 15 millimeters.

Computerized scanning systems are well-known in the art. See, e.g., Zyoptix Custom Wavefront LASIK (Bausch & Lomb, Rochester, N.Y.). The scanning system can be implemented using one or more computer systems. An exemplary computer system can include software, monitor, cabinet, keyboard, and mouse. The cabinet can house familiar computer components, such as a processor, memory, mass storage devices, and the like. Mass storage devices may include mass disk drives, floppy disks, Iomega ZIP™ disks, magnetic disks, fixed disks, hard disks, CD-ROMs, recordable CDs, DVDs, DVD-R, DVD-RW, Flash and other nonvolatile solid-state storage, tape storage, reader, and other similar media, and combinations of these. A binary, machine-executable version, of the software of the present invention may be stored or reside on mass storage devices. Furthermore, the source code of the software of the present invention may also be stored or reside on mass storage devices (e.g., magnetic disk, tape, or CD-ROM). Furthermore, a computer system can include subsystems such as central processor, system memory, input/output (I/O) controller, display adapter, serial or universal serial bus (USB) port, network interface, and speaker. The present invention may also be used with computer systems with additional or fewer subsystems. For example, a computer system could include more than one processor (i.e., a multiprocessor system) or a system may include a cache memory. The beam may be guided in any shape or pattern, including, without limitation, a spiral pattern, a raster pattern, or a segregated regional pattern.

Figure 2:
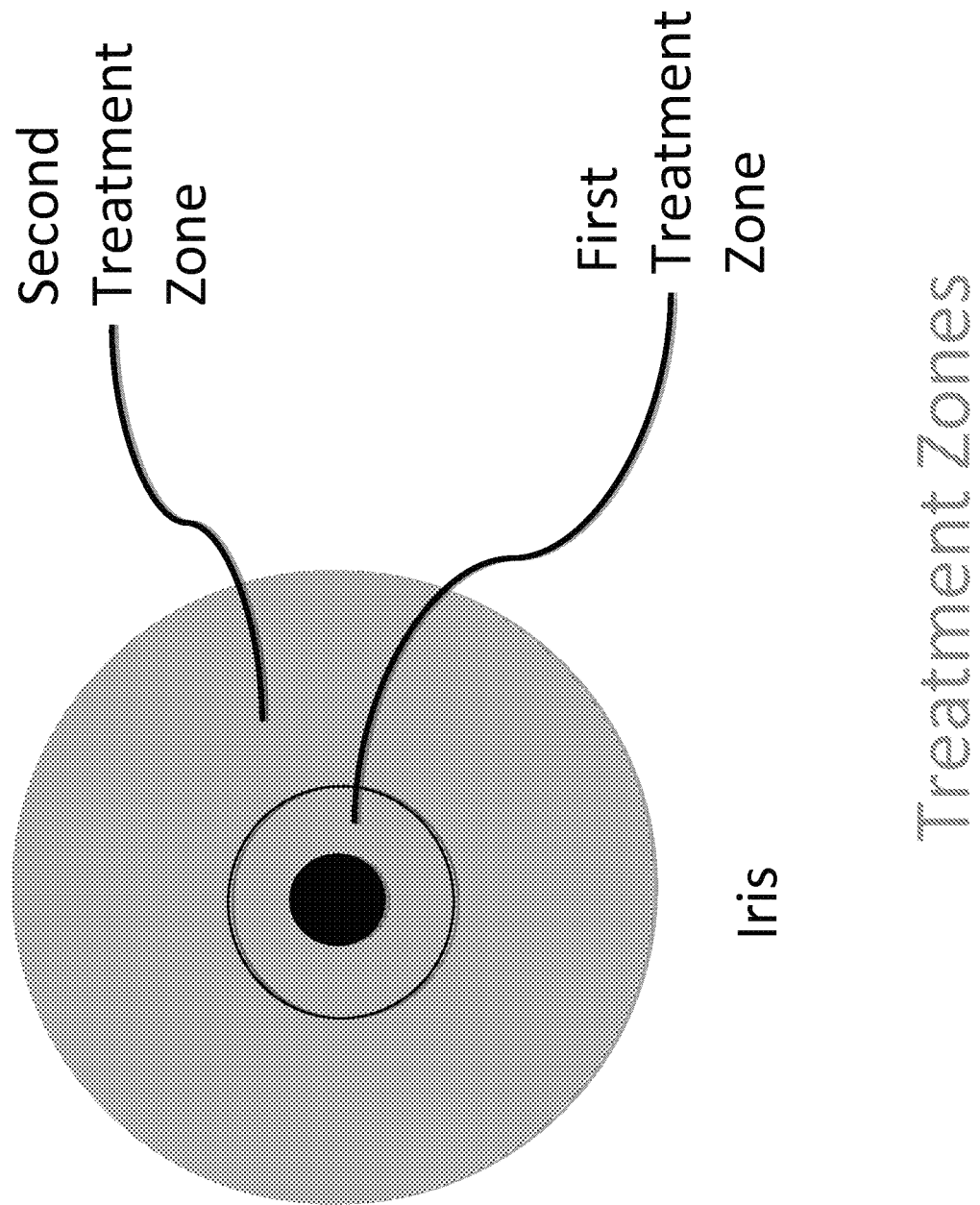
FIG. 2 shows aspects of an embodiment of the invention wherein the anterior iris is divided into two treatment zones, each zone being concentric to the pupil.

In another version of the foregoing embodiment, the anterior iris is divided into two treatment zones, each zone being concentric to the pupil. See FIG. 2. The first treatment zone extends approximately from the outer periphery of the pupillary constrictor muscles to the outer periphery of the pupil. The second treatment zone extends approximately from the limbus to the outer periphery of the pupillary constrictor muscles. The computerized scanning system applies the laser beam first to the first treatment zone, in a spiral pattern, from the outer periphery to the inner periphery, and second to the second treatment zone, in a spiral pattern, from the outer periphery to the inner periphery.

In another embodiment of the invention, the electromagnetic radiation comprises sound waves. In one version of this embodiment, the electromagnetic radiation generator is a SASER, and the electromagnetic radiation pathway is a SASER beam. The computerized scanning system applies the SASER beam to the anterior surface of the iris. The profile of the SASER beam is Gaussian, such that the beam profile converges to a focal point and then diverges from that focal point. See FIG. 1. Due to the profile of the SASER beam, the energy density at the anterior iris is greater than the energy density at the fundus. In independent alternate versions of this embodiment, the divergence angle of the beam is 1.0-2.5 degrees, 2.5-5.0 degrees, 5.0-7.5 degrees, 7.5-10.0, 10.0-12.5 degrees, 12.5-15.0 degrees, 15.0-20.0 degrees, or greater than 20.0 degrees. See FIG. 1. In further independent alternate versions of this embodiment, the spot produced by the SASER beam on the anterior surface of the iris has a diameter of 1-10 microns, 10-50 microns, 50-100 microns, 100-200 microns, 200-500 microns, 500-1,000 microns, and 1,000 microns to 15 millimeters.

In independent alternate embodiments of the invention, the electromagnetic radiation is applied to a percentage of the total anterior surface area of the iris equal to 1-25%, 25-50%, 50-75%, or 75-100%.

Figure 3:
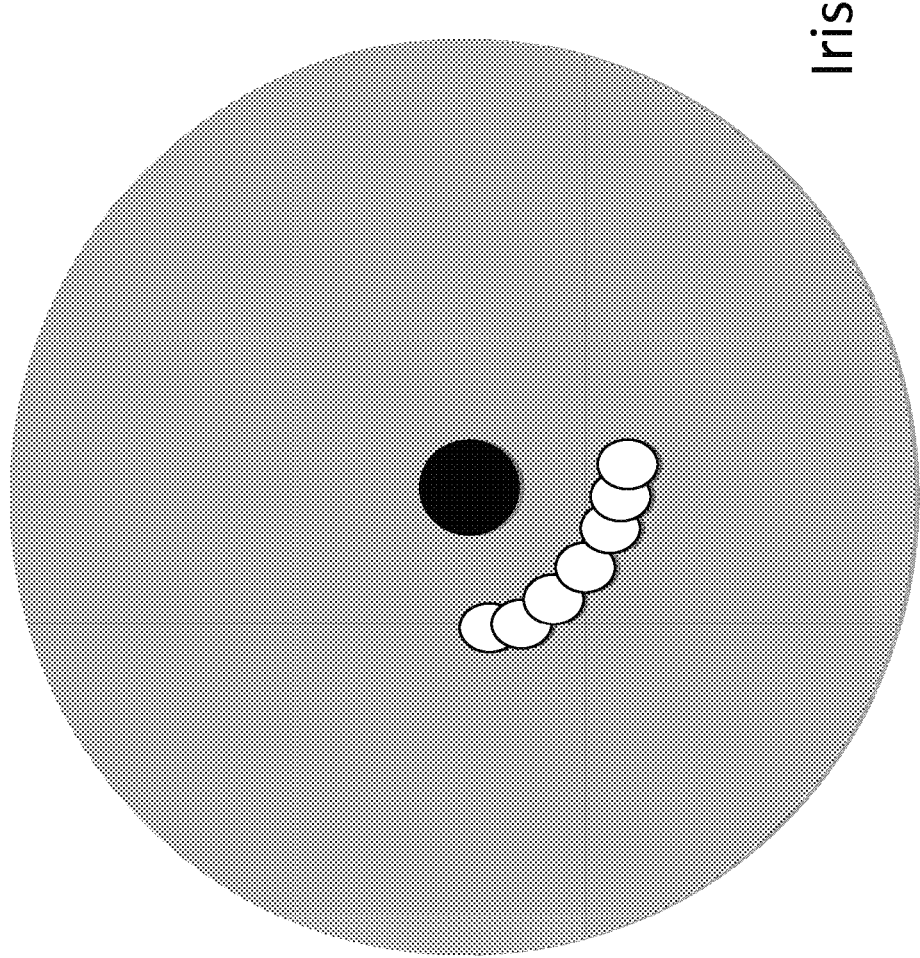
FIG. 3 shows aspects of an embodiment of the invention wherein an application of electromagnetic radiation overlaps a previous application of electromagnetic radiation.
Figure 4:
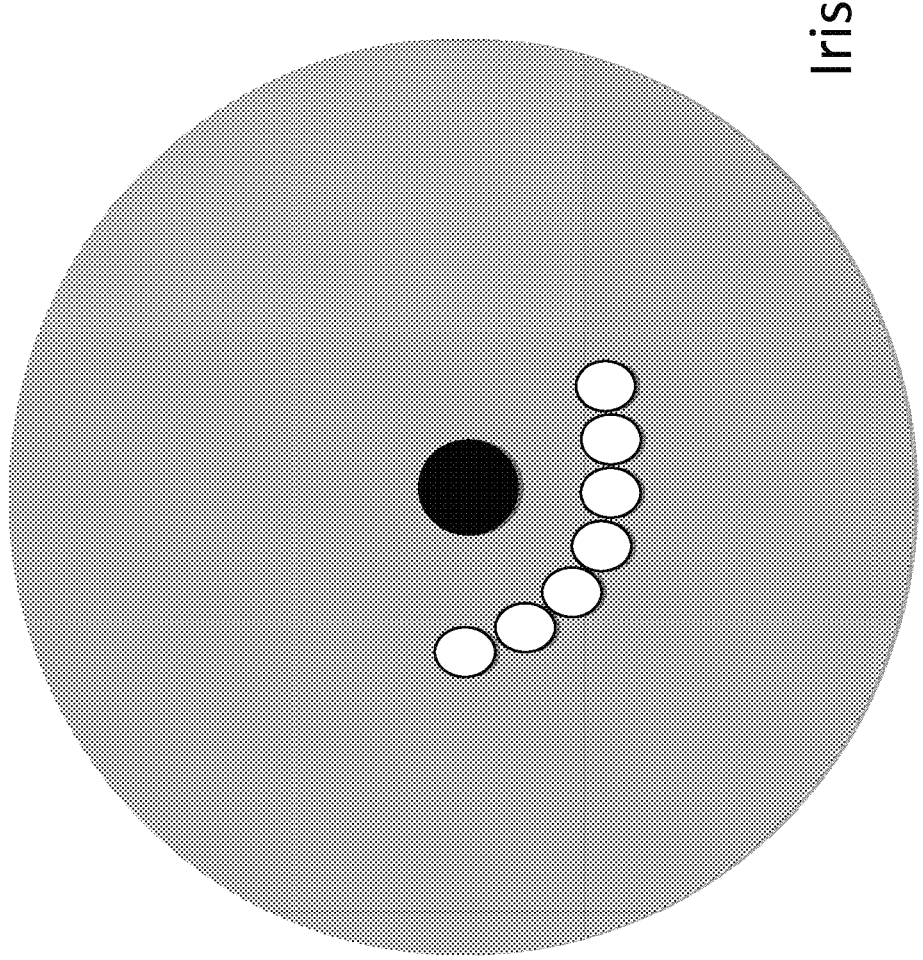
FIG. 4 shows aspects of an embodiment of the invention wherein electromagnetic radiation is applied in a manner that does not overlap any previous application of electromagnetic radiation.
Figure 5:
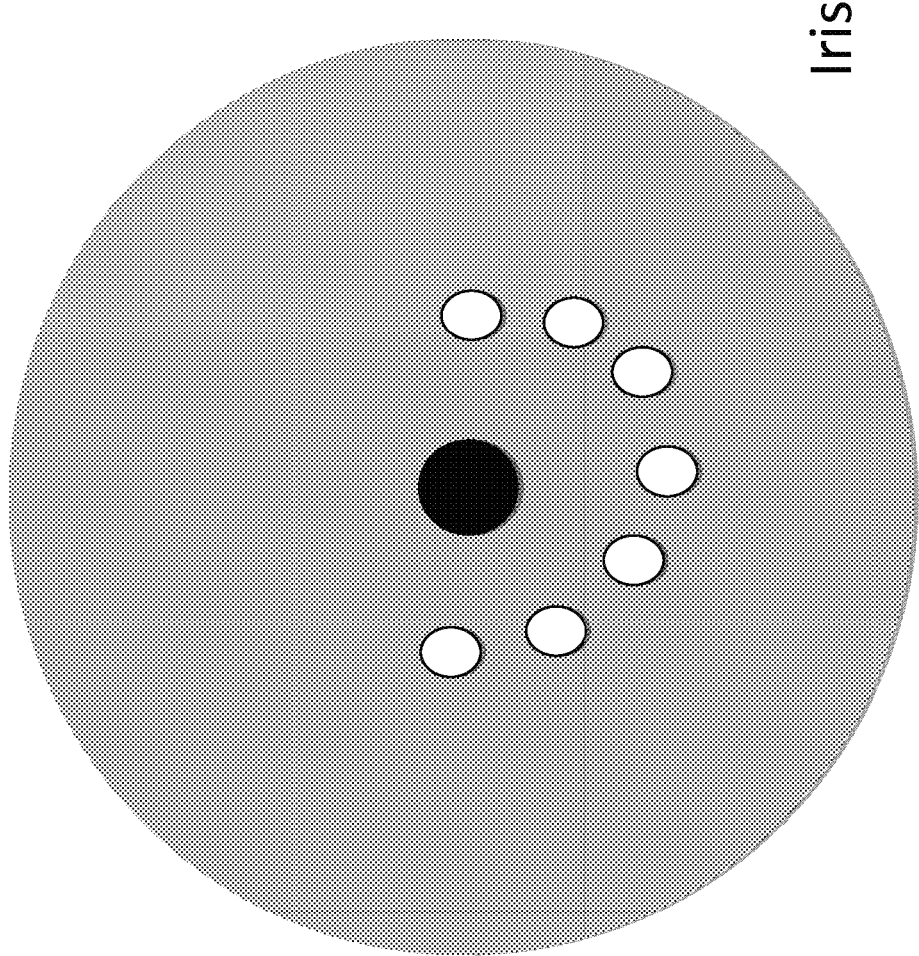
FIG. 5 shows aspects of an embodiment of the invention wherein electromagnetic radiation is applied in a manner that leaves an area of untreated iris between said application and all previous applications of electromagnetic radiation.

In another embodiment of the invention, an application of electromagnetic radiation overlaps a previous application of electromagnetic radiation within a 24-hour period. See FIG. 3. In the laser embodiment above, for example, a laser spot is applied in a manner that overlaps a previously applied laser spot within a 24-hour period. In further independent alternate versions of this embodiment, a spot overlaps a previously applied spot within a 24-hour period by a percentage of the area of the previous spot equal to 0-10%, 10-20%, 20-30%, 30-40%, 40-50%, 50-60%, 60-70%, 70-80%, 80-90%, or 90-100%. In another embodiment, electromagnetic radiation is applied in a manner that does not overlap any previous application of electromagnetic radiation within a 24-hour period. See FIG. 4. In the laser embodiment above, a laser spot is applied in a manner that does not overlap any previously applied laser spot within a 24-hour period. In yet another embodiment, an application of electromagnetic radiation leaves an area of untreated iris between said application and all previous applications of electromagnetic radiation within a 24-hour period. See FIG. 5. In the laser embodiment above, a laser spot is applied in a manner that leaves an area of untreated iris between such spot and all previously applied laser spots within a 24-hour period. In further independent alternate versions of this embodiment, a spot is applied in a manner that leaves a distance between such spot and all previously applied laser spots within a 24-hour period equal to 1-10 microns, 10-microns, 50-100 microns, 100-200 microns, 200-500 microns, 500-1,000 microns, and 1,000 microns to 15 millimeters. And in a further embodiment, some electromagnetic radiation applications overlap previous applications, and others do not, in a 24-hour period. In the laser embodiment above, some laser spots overlap previous laser spots, and others do not, within a 24-hour period.

Figure 6:
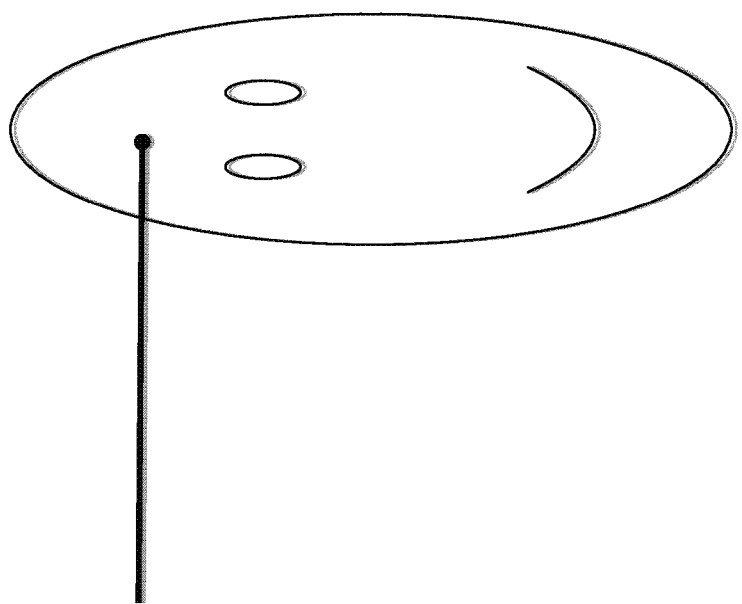
FIG. 6 shows aspects of an embodiment of the invention wherein a novel head fixation target is used to restrict head movement of the head during the procedure.

In another embodiment of the invention, the device includes an apparatus to restrict movement of the head during the procedure. In one version of this embodiment, movement of the head is restricted using a surgical head restrain. Surgical head restrains are well-known in the art. Examples include the Surgical Head Restraint System (RTP Company, Winona, Minn.) and the head restrain straps (Equip. No. BF039) for use with the Cmax Shoulder Chair (Equip. No. BF594) (Steris Corporation, Mentor, Ohio). In another version of this embodiment, a bite bar is used to restrict movement of the head during the procedure. Use of a bite bar to restrict head movement is well-known in the art, including the use of a bite bar during brain imaging. See, e.g., Menon, et al., Design and efficacy of a head-coil bite bar for reducing movement-related artifacts during functional MRI scanning, 29 Behav. Res. Meth., Instr., & Comp. 589-94 (1997). In yet another version of this embodiment, a head fixation target is used to restrict head movement of the head during the procedure. The head fixation target is a novel device invented by Applicant. It utilizes one or more rods, bars, or straps, made of any metal, fabric, plastic, or any other material, material, to apply pressure to predetermined points on the patient's head, thereby providing feedback to the patient with respect to any movement. See FIG. 6.

In another embodiment of the invention, the device includes an apparatus to restrict movement of the eye during the procedure. In one version of this embodiment, movement of the eye is restricted using a suction ring. Ophthalmic suction rings are well-known in the art. See Corneal Surgery: Theory, Technique, and Tissue 722 (Brightbill, ed., 4th ed., 2009). In another version, movement is restricted using a gaze fixation target. Gaze fixation is well-known in the art. See Šimonová, Ocular and orbital legions, in Principles and practice of stereotactic radiosurgery 593 (Chin & Regine, eds., 2008). Gaze fixation can utilize any object of fixation, including, without limitation, a three-dimensional object, a two-dimensional image, or a light. In one novel variation on this version of this embodiment invented by Applicant, a light source is placed at the end of a tube, such that the patient must look through the tube in order to see the light source. In addition to providing a gaze fixation target, this variation also provides a head fixation target because if the patient's moves off axis, the light source will no longer be visible. In another novel variation on this version of this embodiment invented by Applicant, the light produced by the light source changes colors during the procedure. The light might, for example, cycle among amber, red, green, white, and yellow. A color-changing fixation target is less likely to induce involuntary saccadic or other movement of the eye in order to refresh the image on the retina or, alternatively, the discomfort that comes with suppressing such movement. See Tomimatsu. The "rotating snakes" in smooth motion do not appear to rotate, 39 Perception 721-24 (2010). In another novel variation on this version of this embodiment invented by Applicant, the light produced by the light source changes intensity during the procedure. The light might, or example, cycle among bright, medium, and dim. An intensity-changing fixation target is also less likely to induce involuntary saccadic or other movement of the eye in order to refresh the image on the retina or, alternatively, the discomfort that comes with suppressing such movement. See id. at 721-24. In still another novel variation on this version of this embodiment invented by Applicant, the fixation target comprises a moving image, which image may be animated or live action, in color or in black and white, in two- or three-dimensions. A moving image fixation target is also less likely to induce involuntary saccadic or other movement of the eye in order to refresh the image on the retina or, alternatively, the discomfort that comes with suppressing such movement. See id. at 721-24. Any of these embodiments, variations, or versions may be placed in front of the treated eye or the fellow eye during the procedure in order to achieve fixation of the treated eye.

In another embodiment of the invention, the device includes an apparatus to detect movement of the eye during treatment. In one version of this embodiment, active eye tracking is used, whereby movement of the eye is identified, and the electromagnetic pathway is moved to correspond to the movement of the eye. These movements may consist of shifts along the anterior surface of the iris (along the so-called x-y plane), shifts in depth (along the so-called z axis), rotations around the orbital axis, or otherwise. Active eye tracking is well-known in the art. See, e.g., SMI Surgery Guidance (SensoMotoric Instruments GmbH, Teltow, Germany). In another version of this embodiment, passive eye tracking is used, whereby movement of the eye is identified, and the electromagnetic radiation pathway is terminated or suspended. In a novel variation on this version of this embodiment invented by Applicant, movement of the eye is identified, and the electromagnetic radiation pathway is suspended until the eye returns to its previous position or assumes some other desired position, at which time the electromagnetic radiation pathway is resumed. In independent alternate variations on these versions of this embodiment, the electromagnetic radiation pathway is terminated or suspended by (a) terminating or suspending the power to the electromagnetic radiation source, (b) turning off the electromagnetic radiation source, (c) redirecting the electromagnetic radiation pathway away from the target area, (d) utilizing a shutter, baffle, shield, or other occluding device to interrupt the electromagnetic radiation pathway, or (e) utilizing a optical modulator (such as an acousto-optical modulator or an electro-optical modulator) or other energy modulator to interrupt the electromagnetic radiation pathway.

In another embodiment of the invention, the device includes infrared iris transillumination technology. This technology is well-known in the art. See Chan, Digital Camera System to Perform Infrared Photography of Iris Transillumination, 11 J. Glaucoma 426-28 (2002). Many eye-tracking technologies use the pupil to track eye movement. In dark irides, however, the pupil can be difficult to locate. Accordingly, in a novel variation on this embodiment invented by Applicant, infrared iris transillumination is used to more easily identify the pupil in dark irides.

In another embodiment of the invention, the device includes an apparatus to measure the refractive indexes of the eye and adjusts the application of the light to take into account the refraction of the light during treatment. In one version of this embodiment, the apparatus measures the depth of the anterior chamber of the eye and adjusts the application of the light to take into account the refraction of the light during treatment. Apparatus for measuring anterior chamber depth are well-known in the art. Examples include the Lenstar® technology from Haag-Streit AG (Koeniz, Switzerland) and the IOLMaster® technology from Carl Zeiss Meditec AG (Jena, Germany). In another version of this embodiment, the apparatus measures the shape of the cornea and adjusts the application of the light to take into account the refraction of the light during treatment. Apparatus for measuring anterior chamber depth are well-known in the art. Examples include the Pentacam® HR technology from OCULUS Optikgeräte GmbH (Wetzlar, Germany) and the ATLAS™ 9000 Corneal Topography System from Carl Zeiss Meditec AG (Jena, Germany).

One of ordinary skill in the art would recognize many other variations, modifications, and alternatives. The above examples are merely illustrations, which should not unduly limit the scope of the claims herein. It is also understood that the examples and embodiments described herein are for illustrative purposes only and that various modifications or changes in light thereof will be suggested to persons skilled in the art and are to be included within the spirit and purview of this application and scope of the appended claims.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

I claim:

1. A method for preventing accidental overexposure of electromagnetic radiation to a posterior portion of a human eye while applying electromagnetic radiation to an iris of the human eye to perform a color changing operation by delivering the electromagnetic radiation such that an energy density at the iris is greater than an energy density at the posterior portion of the human eye, the method comprising:

generating, using an electromagnetic radiation generator, a laser beam; and applying, using a computerized scanning system, the laser beam to a surface area of an anterior surface of the iris, wherein the surface area comprises at least 25% of the anterior surface, wherein the laser beam produces a spot on the surface area, wherein the laser beam converges at a focal point and then diverges from the focal point at a divergence angle of 1 to 20 degrees from the focal point, wherein at least a portion a convergence of the laser beam occurs anterior to the surface area, and wherein at least a portion of a divergence of the laser beam occurs posterior to the surface area.

2. The method of claim 1, wherein a diameter of the spot is 1 to 10 microns.

3. The method of claim 1, wherein a diameter of the spot is 10 to 50 microns.

4. The method of claim 1, wherein a diameter of the spot is 50 to 100 microns.

5. The method of claim 1, wherein a diameter of the spot is 100 to 200 microns.

6. The method of claim 1, wherein a diameter of the spot is 200 to 500 microns.

7. The method of claim 1, wherein a diameter of the spot is 500 to 1000 microns.

8. The method of claim 1, wherein a diameter of the spot is 1000 microns to 15 millimeters.

9. The method of claim 1, wherein the divergence angle of the laser beam is 1.0 to 2.5 degrees.

10. The method of claim 1, wherein the divergence angle of the laser beam is 2.5 to 5.0 degrees.

11. The method of claim 1, wherein the divergence angle of the laser beam is 5.0 to 7.5 degrees.

12. The method of claim 1, wherein the divergence angle of the laser beam is 7.5 to 10.0 degrees.

13. The method of claim 1, wherein the divergence angle of the laser beam is 10.0 to 12.5 degrees.

14. The method of claim 1, wherein the divergence angle of the laser beam is 12.5 to 15.0 degrees.

15. The method of claim 1, wherein the divergence angle of the laser beam is 15.0 to 20.0 degrees.

16. The method of claim 1, wherein a shape of the spot comprises square, rectangular, circular, elliptical, triangular, trapezoidal, or torus shape.

17. The method of claim 1, wherein the surface area comprises 25% to 50% of the anterior surface.

18. The method of claim 1, wherein the surface area comprises 50% to 75% of the anterior surface.

19. The method of claim 1, wherein the surface area comprises 75% to 100% of the anterior surface.

20. A non-transitory, computer-readable medium comprising instructions that, when executed by one or more processors, cause operations comprising:
generating, using an electromagnetic radiation generator, a laser beam to perform a color changing operation; and
applying, using a computerized scanning system, the laser beam to a surface area of an anterior surface of an iris, wherein the surface area comprises at least 25% of the anterior surface of the iris, wherein the laser beam produces a spot on the surface area, wherein the laser beam converges at a focal point and then diverges from the focal point at a divergence angle of 1 to 20 degrees from the focal point, wherein at least a portion a convergence of the laser beam occurs anterior to the surface area, and wherein at least a portion of a divergence of the laser beam occurs posterior to the surface area.

21. The non-transitory, computer-readable medium of claim 20, wherein a diameter of the spot is 1 to 10 microns.

22. The non-transitory, computer-readable medium of claim 20, wherein a diameter of the spot is 10 to 50 microns.

23. The non-transitory, computer-readable medium of claim 20, wherein a diameter of the spot is 50 to 100 microns.

24. The non-transitory, computer-readable medium of claim 20, wherein a diameter of the spot is 100 to 200 microns.

25. The non-transitory, computer-readable medium of claim 20, wherein a diameter of the spot is 200 to 500 microns.

26. The non-transitory, computer-readable medium of claim 20, wherein a diameter of the spot is 500 to 1000 microns.

27. The non-transitory, computer-readable medium of claim 20, wherein a diameter of the spot is 1000 microns to 15 millimeters.

28. The non-transitory, computer-readable medium of claim 20, wherein the divergence angle of the laser beam is 1.0 to 2.5 degrees.

29. The non-transitory, computer-readable medium of claim 20, wherein the divergence angle of the laser beam is 2.5 to 5.0 degrees.

30. The non-transitory, computer-readable medium of claim 20, wherein the divergence angle of the laser beam is 5.0 to 7.5 degrees.

31. The non-transitory, computer-readable medium of claim 20, wherein the divergence angle of the laser beam is 7.5 to 10.0 degrees.

32. The non-transitory, computer-readable medium of claim 20, wherein the divergence angle of the laser beam is 10.0 to 12.5 degrees.

33. The non-transitory, computer-readable medium of claim 20, wherein the divergence angle of the laser beam is 12.5 to 15.0 degrees.

34. The non-transitory, computer-readable medium of claim 20, wherein the divergence angle of the laser beam is 15.0 to 20.0 degrees.

35. The non-transitory, computer-readable medium of claim 20, wherein a shape of the spot comprises square, rectangular, circular, elliptical, triangular, trapezoidal, or torus shape.

36. The non-transitory, computer-readable medium of claim 20, wherein the surface area comprises 25% to 50% of the anterior surface.

37. The non-transitory, computer-readable medium of claim 20, wherein the surface area comprises 50% to 75% of the anterior surface.

38. The non-transitory, computer-readable medium of claim 20, wherein the surface area comprises 75% to 100% of the anterior surface.

39. A system comprising:
one or more processors programmed to:
generate, using an electromagnetic radiation generator, a laser beam to perform a color changing operation; and
apply, using a computerized scanning system, the laser beam to a surface area of an anterior surface of an iris, wherein the surface area comprises at least 25% of the anterior surface of the iris, wherein the laser beam produces a spot on the surface area, wherein the laser beam converges at a focal point and then diverges from the focal point at a divergence angle of 1 to 20 degrees from the focal point, wherein at least a portion a convergence of the laser beam occurs anterior to the surface area, and wherein at least a portion of a divergence of the laser beam occurs posterior to the surface area.

* * * * *